United States Patent [19]
Rydell et al.

[11] Patent Number: 5,158,561
[45] Date of Patent: Oct. 27, 1992

[54] MONOPOLAR POLYPECTOMY SNARE WITH COAGULATION ELECTRODE

[75] Inventors: Mark A. Rydell, Golden Valley; John F. Stock, Kensington; John L. Zenk, Hutchinson, all of Minn.

[73] Assignee: Everest Medical Corporation, Minneapolis, Minn.

[21] Appl. No.: 856,306

[22] Filed: Mar. 23, 1992

[51] Int. Cl.$^5$ .............................................. A61B 17/00
[52] U.S. Cl. ...................... 606/113; 128/642; 606/29; 606/37; 606/39; 606/40; 606/47; 606/49; 606/110
[58] Field of Search ................ 128/783, 788, DIG. 22, 128/639, 642, 644; 604/20, 22; 606/1, 28, 29, 32, 37, 39, 40, 45–52, 110, 113, 108

[56] References Cited

U.S. PATENT DOCUMENTS

| | | | |
|---|---|---|---|
| 4,311,143 | 1/1982 | Komiya | 606/47 |
| 4,326,530 | 4/1982 | Fleury | 606/47 |
| 4,493,320 | 1/1985 | Treat . | |
| 4,682,967 | 2/1987 | Bales et al. | 606/39 |
| 4,905,691 | 3/1990 | Rydell | 606/47 |
| 5,026,371 | 6/1991 | Rydell et al. | 606/113 |
| 5,071,419 | 12/1991 | Rydell et al. | 606/50 |
| 5,078,716 | 1/1992 | Doll | 606/47 |
| 5,080,660 | 1/1992 | Buelna | 606/50 |
| 5,084,054 | 1/1992 | Bencini et al. | 606/127 |
| 5,085,659 | 2/1992 | Rydell | 606/48 |

FOREIGN PATENT DOCUMENTS

| | | | |
|---|---|---|---|
| 2808546 | 8/1978 | Fed. Rep. of Germany | 606/47 |
| 3220940 | 12/1983 | Fed. Rep. of Germany | 606/47 |
| 2501034 | 9/1982 | France | 606/50 |

Primary Examiner—Stephen C. Pellegrino
Assistant Examiner—Glenn Dawson
Attorney, Agent, or Firm—Haugen and Nikolai

[57] ABSTRACT

A monopolar electrosurgical instrument for excising polyps from the gastrointestinal tract comprises an elongated flexible plastic tube having a first monopolar electrode mounted a small predetermined distance from the distal end of the tubular member and a conductive wire loop affixed to a pull-wire, the pull-wire extending through the lumen of the tubular member and being connected at its proximal end to a plunger-type handle whereby the loop can be opened and closed by extending and retracting the loop relative to the distal end of the tubulr member. By incorporating both the surface electrode and the loop on the same instrument, polyps may be severed electrosurgically using the snare and the wound then immediately cauterized using the surface electrode, thus obviating the need to do an instrument exchange in the endoscope to accomplish both functions.

3 Claims, 1 Drawing Sheet

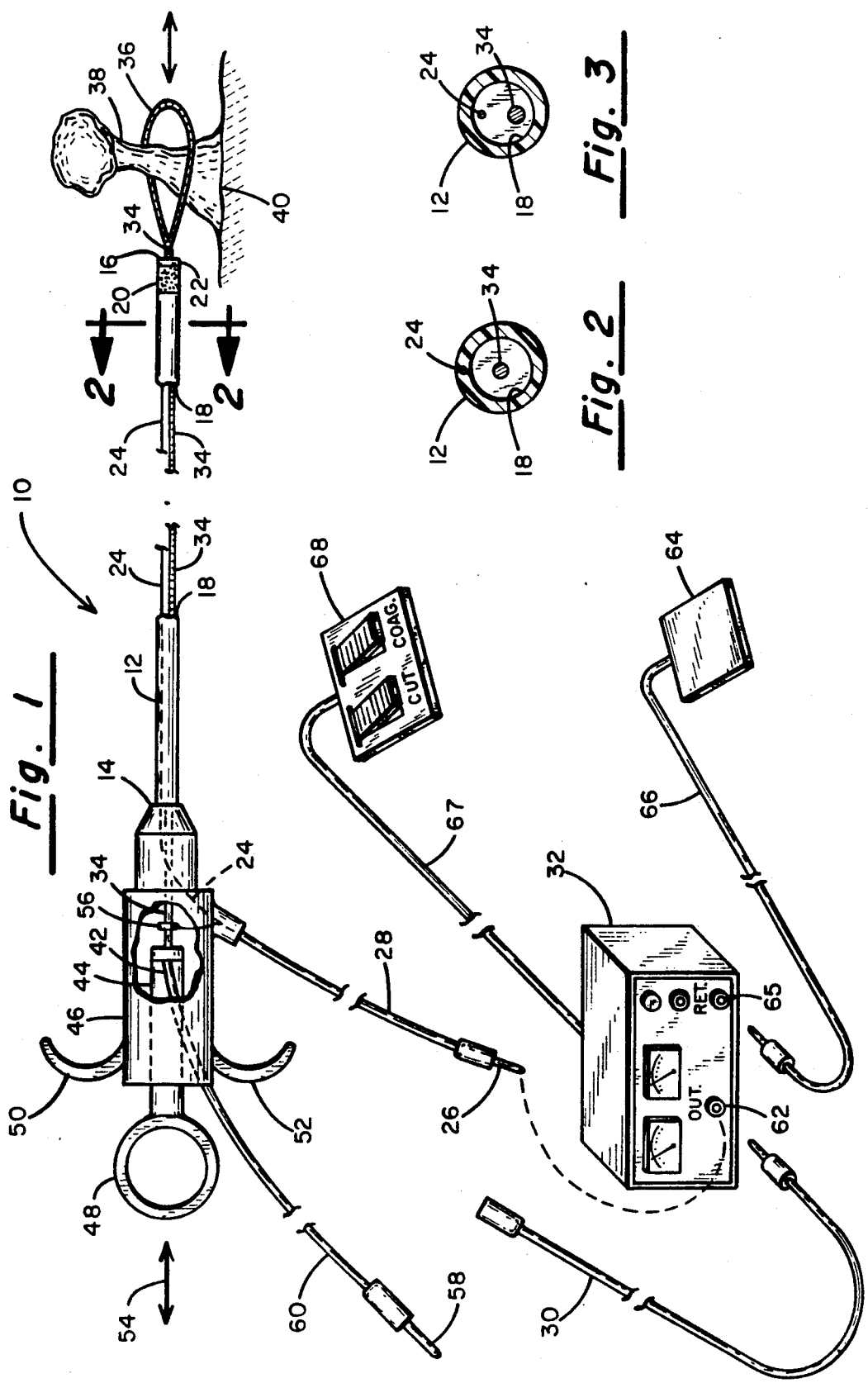

MONOPOLAR POLYPECTOMY SNARE WITH COAGULATION ELECTRODE

BACKGROUND OF THE INVENTION

I. Field of the Invention

This invention relates generally to electrosurgical apparatus, and more particularly to a monopolar polypectomy snare incorporating means for effecting coagulation at the site of the polyp removal.

II. Discussion of the Prior Art

Various electrosurgical devices are known in the art which can be routed through endoscope into the gastrointestinal tract for removing polyps from the walls of the tract. The Treat U.S. Pat. No. 4,493,320 describes a bipolar electrocautery surgical snare capable of performing the endoscopic removal of growths, such as polyps, within a body cavity. That device comprises an elongated flexible insulating double lumen tubular member through which a pair of insulated conductors pass the distal end segments of these two conductors and are stripped free of insulation and are joined together by a small insulating button, thus forming a bipolar pair. When a pedunculated polyp is lassoed by the snare and then the snare wires are retracted in the proximal direction to close the loop, a point is reached where the tissue comprising the stalk of the polyp bridges the gap between the two electrodes and is cut off. If properly manipulated, any bleeding is cauterized.

The Komiya U.S. Pat. No. 4,311,143 describes an alternative arrangement for a bipolar polypectomy snare in which the entire loop comprising the snare is at the same electrical potential and a bipolar mating electrode is affixed to the distal end of the tubular body of the snare device and is separately coupled by a conductor to a high frequency generator. In this arrangement, the ring or surface electrode at the distal tip of the tubular body forms one electrode while the snare comprises the second electrode. Again, by looping the snare about the polyp and then retracting the loop into the distal end of the tubular body, the stem of the polyp is made to bridge the two electrodes to sever the polyp. By proper application of the high frequency current as the snare is being drawn about the stalk of the polyp, cauterization of the wound is accomplished.

The present invention differs from the prior art as represented by the Treat and Komiya patents discussed above in that it is designed for monopolar operation. In a monopolar device, rather than positioning two electrodes in close proximity to one another and applying a voltage between them, a large area body plate is made to intimately engage the leg or buttocks of the patient and it serves as the return electrode. The active electrode is affixed to the surgical instrument and is connected to the electrosurgical generator. In designing prior art monopolar polypectomy snares, the only active electrode on the instrument has been the loop projecting from the distal end of the instrument's tubular body. Thus, a physician could cut with the loop, but its ability to coagulate at the same time has been marginal, at best. A surgeon using the monopolar instrument would be required to do an instrument exchange in the endoscope once the polyp is severed in order to provide a separate instrument for coagulating the tissue and effecting hemostasis. The delay in making the instrument switch will often result in sufficient bleeding and obscuring of the optical system of the endoscope, thereby requiring further steps of irrigating and aspirating the surgical site to effectively clean off the endoscope optics.

It is the primary object of the present invention to provide a monopolar snare type electrosurgical instrument which also embodies a monopolar electrode for coagulating tissue by electrodesiccation.

SUMMARY OF THE INVENTION

In accordance with the present invention, the monopolar electrosurgical instrument comprises an elongated insulating plastic tube having a proximal end, a distal end and a lumen extending therebetween. Affixed to the outer surface of the insulating tubular member is a metallic sleeve positioned a small, predetermined distance proximal of the distal end of the tube. This ring-type surface electrode is connected by a conductive wire, which may extend either through the wall of the tubular member or through its lumen, to an electrical jack which is designed to mate with the output terminal of a conventional monopolar electrosurgical generator. Extending through the lumen of the elongated flexible tube is a conductor which also functions as a pull-wire. Electrically and mechanically attached to the distal end of that conductor is a conductive wire loop, also comprising a monopolar electrode. The pull-wire is operatively coupled to a terminal jack adapted to mate with the output terminal of the electrosurgical generator. The pull-wire is affixed to a slide or plunger assembly attached to the proximal end of the elongated plastic tube, whereby manipulation of the plunger allows the loop to be retracted into the distal end of the plastic tube and thereby closed or extended out therefrom to open the loop.

When it is desired to first excise a polyp, the plunger is advanced in the distal direction to cause the loop electrode to spread open, allowing it to be positioned over the polyp to be removed. Once the snare is disposed about the stalk of the polyp and the electrical jack associated therewith is assembled to the output terminal of the electrosurgical generator, the surgeon may draw back on the plunger to retract the loop relative to the distal end of the elongated flexible tube and, at the same time, by manipulating a foot switch control on the electrosurgical generator cause a CUT or COAG current to flow through the loop electrode, the tissue to be cut and return to the body plate. Rather than now exchanging the instrument for a electrocoagulator, the surgeon need only plug the COAG jack of the device into the electrosurgical generator which takes only a few seconds, thereby disabling the loop electrode and energizing the surface electrode, which can now be used for desiccating and thereby coagulating bleeding blood vessels. Because of the rapidity with which this change can be made, very little blood flow is experienced.

DESCRIPTION OF THE DRAWINGS

The foregoing features, objects and advantages of the invention will become more apparent to those skilled in the art from the following detailed description of a preferred embodiment, especially when considered in conjunction with the accompanying drawings in which like numerals in the several views refer to corresponding parts.

FIG. 1 is a perspective view of the monopolar electrosurgical polypectomy snare;

FIG. 2 is a cross-sectional view taken along the line 2—2 in FIG. 1; and

FIG. 3 is a cross-sectional view like that of FIG. 2 but in accordance with an alternative way of routing the electrical conductors.

DESCRIPTION OF THE PREFERRED EMBODIMENT

Referring to FIG. 1, there is indicated generally by numeral 10 a monopolar electrosurgical instrument incorporating the features of the present invention. It is seen to comprise an elongated, flexible tube 12, preferably made from a suitable medical grade plastic, such as polyurethane, polyethylene or Teflon. It has an outside diameter sufficiently small to allow it to fit through the working lumen of an endoscope-type device. The tube 12 has a proximal end 14, a distal end 16 and a lumen 18 extending therebetween. A metallic ring-type surface electrode 20 is mounted near the distal end 16 of the tube 12 but is disposed proximally a short predetermined distance from the distal end to leave a small segment of insulating tubing 22 exposed at the distal end. With reference to FIG. 2, an electrical conductor 24 extends through the wall surface of the tube 12 and is connected at one end to the surface electrode 20 and at its other end to a male terminal 26 at the end of an elongated electrical cord 28. The male terminal 26 is shaped to mate with the output terminal 62 of an electrosurgical generator 32.

Extending through the lumen 18 of the tube 12 is a pull-wire 34 that is attached to a loop 36 of bare electrically conductive wire. In FIG. 1, the loop 36 is shown as surrounding the stalk 38 of a pedunculated polyp extending outward from the surface of a hollow organ 40 in the gastrointestinal tract. The proximal end of the pull-wire 34 is attached to a plunger 42 mounted in a bore 44 formed in a handle member 46. Affixed to the proximal end of the plunger 42 is a ring 48 into which the thumb of the surgeon may be inserted. Projecting laterally outward from the exterior surface of the handle 46 are finger rests 50 and 52 adapted to receive the forefinger and index finger of the surgeon whereby the thumb can be moved back and forth as represented by the double-headed arrow 54 to cause the loop 36 to be extended outward from the distal end 16 of the tube 12 (as illustrated in FIG. 1) or retracted into the lumen 18 of the tube so as to close the loop 36 about the stalk 38 of the polyp. The pull-wire 34 is electrically connected to the male terminal 58 on the proximal end of the cord 60.

FIG. 3 is included to show that both the pull-wire 34 and the coagulating electrode conductor 24 may both extend through the same lumen 18 of the tube 12, provided the wires are appropriately insulated from one another along their entire length.

Referring again to FIG. 1, in a monopolar electrosurgical set-up, the return electrode comprises a large area body plate 64 which may be connected by an appropriate insulated conductor 66 to the RETURN terminal 68 of the electrosurgical generator 32. Again, the conductor 66 will typically be provided with a male jack which can only mate with the female receptacle 68, thus avoiding possible incorrect hook-up of the instrument and ground plate to the electrosurgical generator.

Because the surface electrode 20 used for electrocoagulation is displaced proximally of the distal end 16 of the instrument and the small insulating segment 22 is thereby defined, the conductive loop or snare 36 remains insulated from the surface electrode 20 at all times.

OPERATION

In operation, the instrument 10 has its elongated, flexible tubular shaft inserted through the working channel of an endoscope, and the endoscope is used to visually located and assess the shape and type of polyp to be removed. In the case of a pedunculated polyp as illustrated, the surgeon will loop the snare 36 about the polyp and then with the appropriate connection made to the output terminal 62 of the electrosurgical instrument through extension cord 30, as the thumb ring 48 is retracted to close the snare 36 about the stalk of the polyp, the lever of the foot-switch 68 is depressed to cause a current to flow through the pull-wire 34 and the snare 36 and, thence, through the tissue of the stalk 38 and to the body plate 64. The CUT or COAG current is sufficient to desiccate and explode the cells abutting the snare, causing the polyp to be severed.

Now, rather than having to retract the cutting instrument from the endoscope and replace it with a coagulation instrument, the physician need only plug in the COAG jack 26 into the terminal 62 through extension cord 30 and again depress the foot-switch 68 to cause the coagulating current to flow through the surface electrode 20 and back to the body plate 64 as the surface electrode 20 is wiped or brushed against the severed blood vessels feeding the polyp to thereby stem the flow of blood. Small polyps can also be burned off with the ring electrode if they are too small to loop with a snare.

The instrument of the present invention can also be used to effectively remove sessile polyps by brushing them with the energized loop and effectively shaving them off the supporting tissue.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical instrument for excising polyps from the gastrointestinal tract comprising:
    (a) an elongated flexible plastic tube of an insulating material having a proximal end, a distal end and a lumen extending therebetween;
    (b) a monopolar coagulating electrode disposed on the outer surface of said plastic tube proximate said distal end but inset a small, predetermined distance proximal of said distal end so that said distal end comprises said insulating material;
    (c) a first electrical conductor extending along the length of said tube from said proximal end and attached to said monopolar coagulating electrode;
    (d) a second electrical conductor extending through said lumen from said proximal end to said distal end and terminating in a monopolar snare loop electrode that can be extended and retracted relative to said distal end of said tube to open and close said monopolar snare loop electrode, respectively;
    (e) means disposed on said proximal end of said plastic tube for selectively extending and retracting said loop electrode; and (f) means adapted to selectively couple either said first electrical conductor or said second electrical conductor to an electrosurgical generator such that only one or the other of said monopolar coagulating electrode or said monopolar snare loop electrode is energized at a time.

2. The electrosurgical instrument as in claim 1 wherein said coagulating electrode comprises a metal band coaxially disposed on the outer surface of said plastic tube.

3. The electrosurgical instrument as in claim 1 wherein said first and second electrical conductors are electrically insulated from one another.

* * * * *